(12) United States Patent
Brosovich et al.

(10) Patent No.: US 7,039,455 B1
(45) Date of Patent: May 2, 2006

(54) APPARATUS AND METHOD FOR REMOVING MAGNETIC RESONANCE IMAGING-INDUCED NOISE FROM ECG SIGNALS

(75) Inventors: John A. Brosovich, Pittsburgh, PA (US); Michael J. Yanniello, Cheswick, PA (US); Albert J. Yarzebinski, Glenshaw, PA (US)

(73) Assignee: Medrad, Inc., Indianola, PA (US)

( * ) Notice: Subject to any disclaimer, the term of this patent is extended or adjusted under 35 U.S.C. 154(b) by 365 days.

(21) Appl. No.: 10/256,976

(22) Filed: Sep. 27, 2002

Related U.S. Application Data

(60) Provisional application No. 60/328,076, filed on Oct. 9, 2001.

(51) Int. Cl.
*A61B 5/0402* (2006.01)
*A61N 5/0425* (2006.01)

(52) U.S. Cl. .................... 600/509; 128/901
(58) Field of Classification Search ........ 600/508–509, 600/521; 607/2, 9, 26; 128/901
See application file for complete search history.

(56) References Cited

U.S. PATENT DOCUMENTS

| | | | | |
|---|---|---|---|---|
| 3,868,947 A | | 3/1975 | Holsinger | 600/382 |
| 4,677,986 A | * | 7/1987 | DeCote, Jr. | 600/510 |
| 4,887,609 A | | 12/1989 | Cole, Jr. | 600/509 |
| 4,991,580 A | | 2/1991 | Moore | 600/509 |
| 4,991,587 A | | 2/1991 | Blakeley et al. | 600/483 |
| 5,025,808 A | * | 6/1991 | Hafner | 600/509 |
| 5,038,785 A | | 8/1991 | Blakeley et al. | 600/484 |
| 5,052,398 A | | 10/1991 | Gober | 600/509 |
| 5,209,233 A | | 5/1993 | Holland et al. | 600/412 |
| 5,217,010 A | | 6/1993 | Tsitlik et al. | 607/9 |
| 5,394,873 A | | 3/1995 | Kraemer et al. | 600/523 |
| 5,411,023 A | | 5/1995 | Morris, Sr. et al. | 600/323 |
| 5,417,221 A | * | 5/1995 | Sickler | 600/509 |
| 5,427,111 A | | 6/1995 | Traub et al. | 600/508 |
| 5,436,564 A | * | 7/1995 | Kreger et al. | 600/411 |
| 5,467,034 A | | 11/1995 | Manlove et al. | 327/63 |
| 5,511,553 A | | 4/1996 | Segalowitz | 600/508 |
| 5,691,641 A | | 11/1997 | Cansell et al. | 324/309 |
| 5,724,967 A | | 3/1998 | Venkalachalam | 600/310 |
| 5,733,247 A | | 3/1998 | Fallon | 600/410 |

(Continued)

FOREIGN PATENT DOCUMENTS

EP 0132785 A2 2/1985

OTHER PUBLICATIONS

Laudon, Michael K., "Minimizing Interference From Magnetic Resonance Imagers During Electrocardiography," IEEE Transactions on Biomedical Engineering, vol. 45, No. 2 (Feb. 1998).

(Continued)

*Primary Examiner*—Carl Layno
(74) *Attorney, Agent, or Firm*—James R. Stevenson

(57) ABSTRACT

An apparatus and method is provided for improving the quality of electrocardiogram (ECG) signals obtained from a patient undergoing magnetic resonance imaging (MRI) wherein the ECG signal has relatively high levels of noise or interference voltages induced on it by changing magnetic fields. The apparatus includes the arrangement of a differential amplifier, a prefilter, a signal limiter (SL) circuit and an intermediate amplifier with an integral low pas filter. The prefilter limits the rise time or high frequency component of the noise or interfering voltages induced on the ECG that are presented to the signal limiter.

18 Claims, 7 Drawing Sheets

U.S. PATENT DOCUMENTS

| | | | | |
|---|---|---|---|---|
| 5,743,859 A | * | 4/1998 | Wodlinger et al. | 600/522 |
| 5,782,241 A | | 7/1998 | Felblinger et al. | 600/509 |
| 5,987,348 A | | 11/1999 | Fischer et al. | 600/413 |
| 6,032,063 A | | 2/2000 | Hoar et al. | 600/372 |
| 6,032,069 A | | 2/2000 | Elgavish et al. | 600/413 |
| 6,052,614 A | | 4/2000 | Morris, Sr. et al. | 600/509 |
| 6,073,039 A | | 6/2000 | Berson | 600/372 |
| 6,148,229 A | | 11/2000 | Morris, Sr. et al. | 600/509 |
| 6,198,285 B1 | | 3/2001 | Kormos et al. | 324/318 |
| 6,201,981 B1 | | 3/2001 | Yarita | 600/372 |
| 6,270,463 B1 | | 8/2001 | Morris, Sr. et al. | 600/549 |

OTHER PUBLICATIONS

Shellock, Frank G., "Monitoring During MRI," Medical Electronics Journal, vol. 17, No. 4, Issue 100 pp. 93-97 (Sep. 1986).

Karlik, S.J., "Patient Anesthesia And Monitoring At A 1.5T MRI Installation," Magnetic Resonance In Medicine 7:210-211 (1988).

Felblinger et al., Restor. of Electrophys. Signals Distorted by Inductive Effects of Mag. Field Gradients During MR Sequences, Magnetic Res. in Medicine 41:715-721 (1999).

* cited by examiner

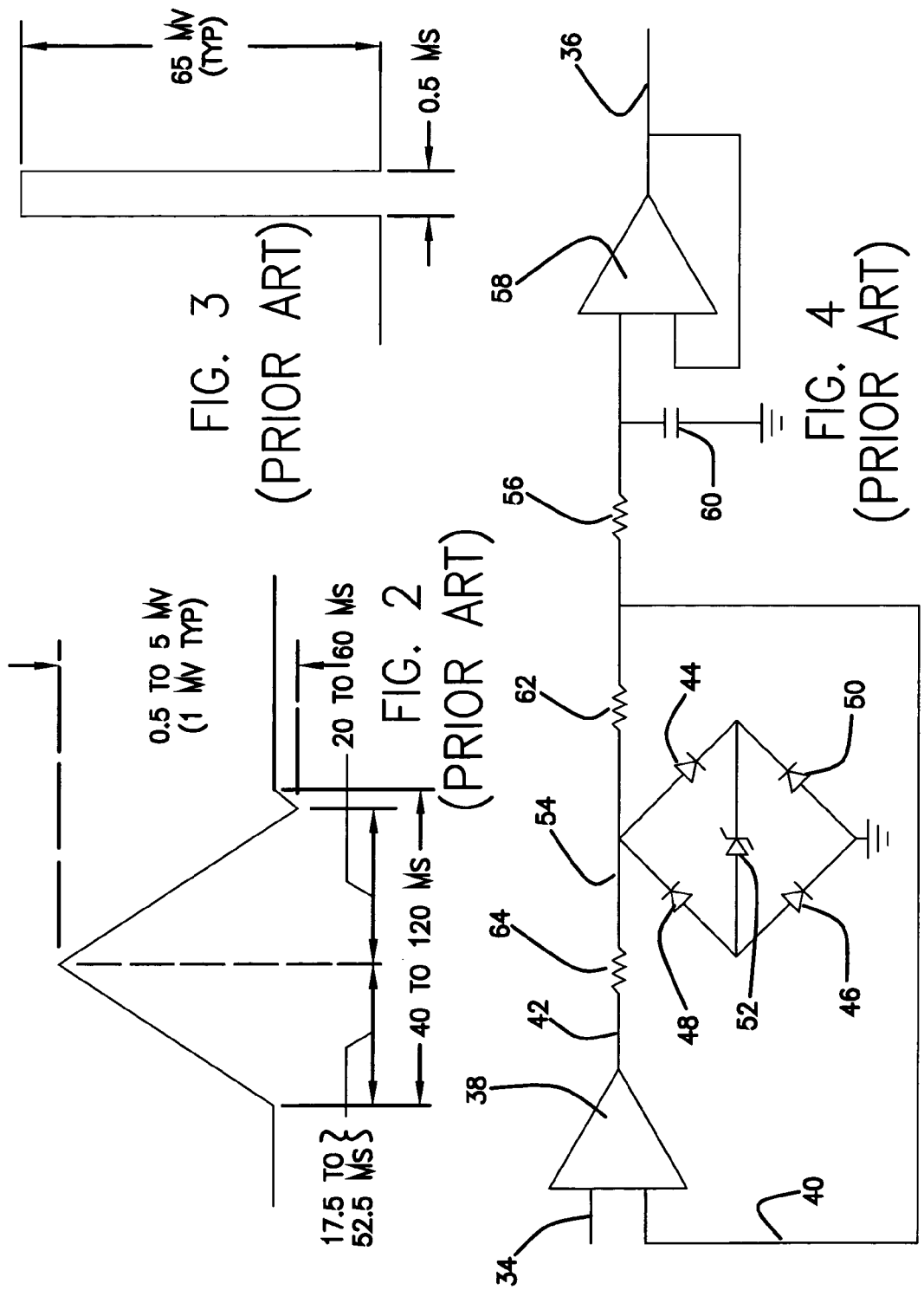

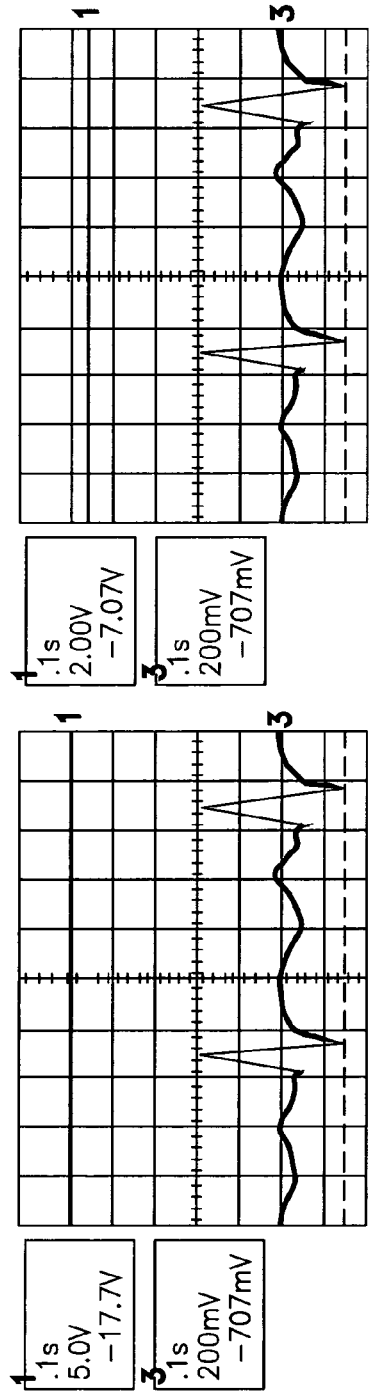
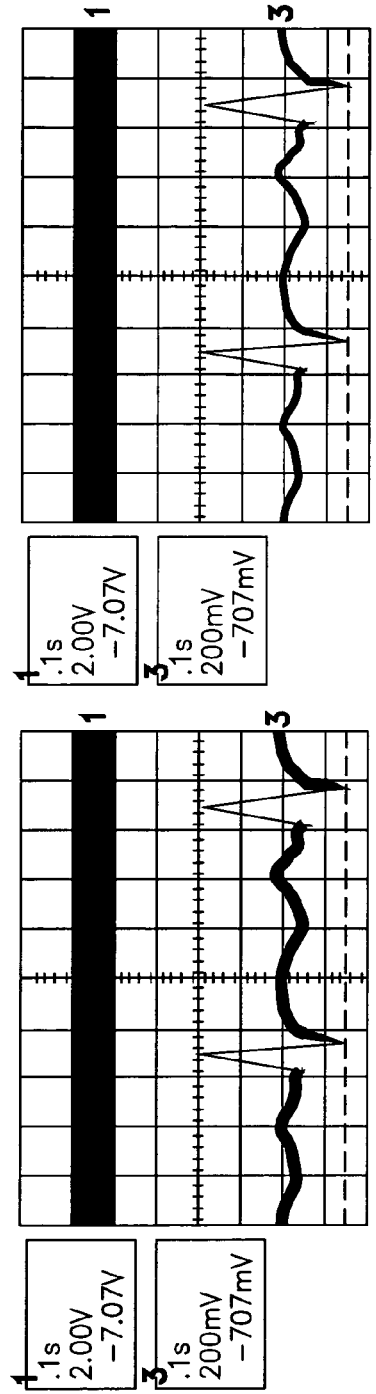
Figure 6A, 0mV noise, no prefilter
Figure 6E, 0mV noise, with prefilter
Figure 6B, 20mV noise, no prefilter
Figure 6F, 20mV noise, with prefilter

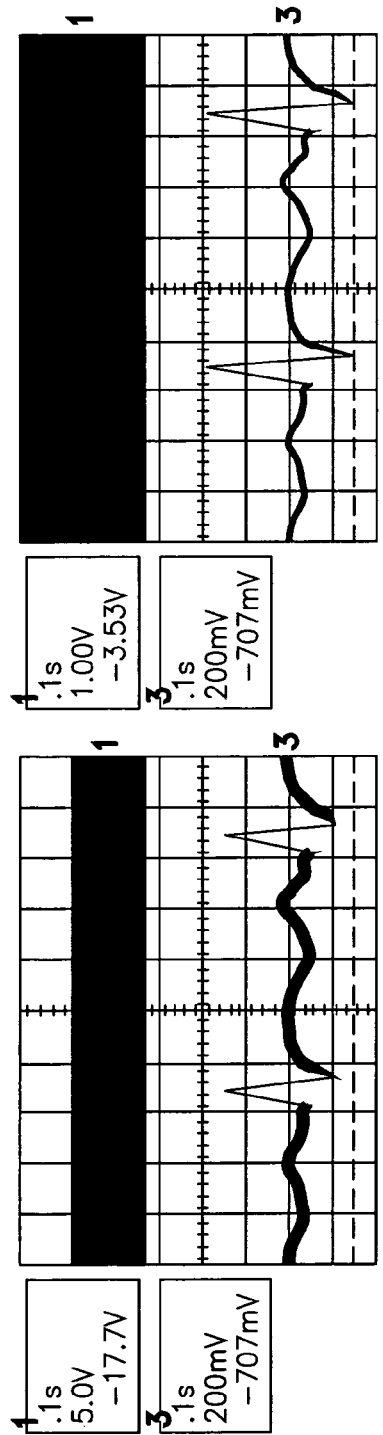
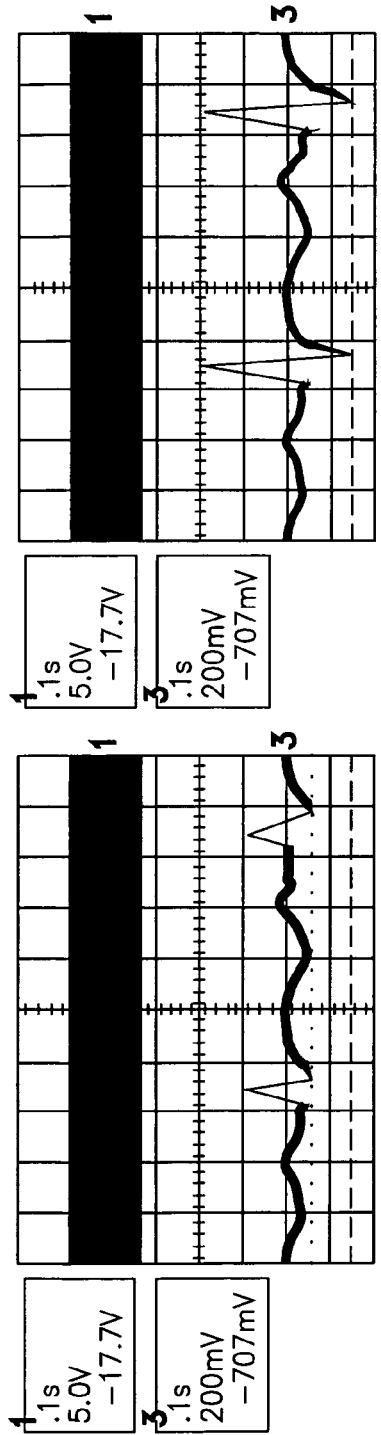

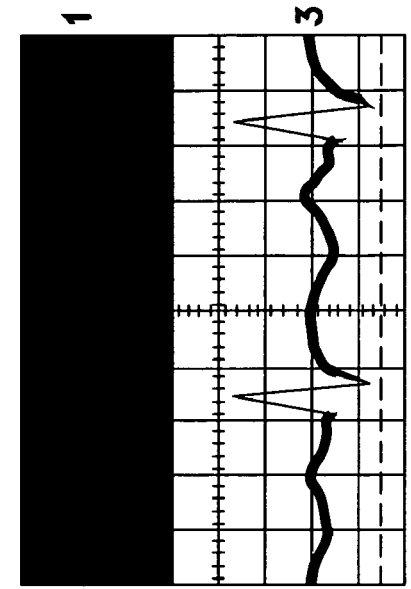
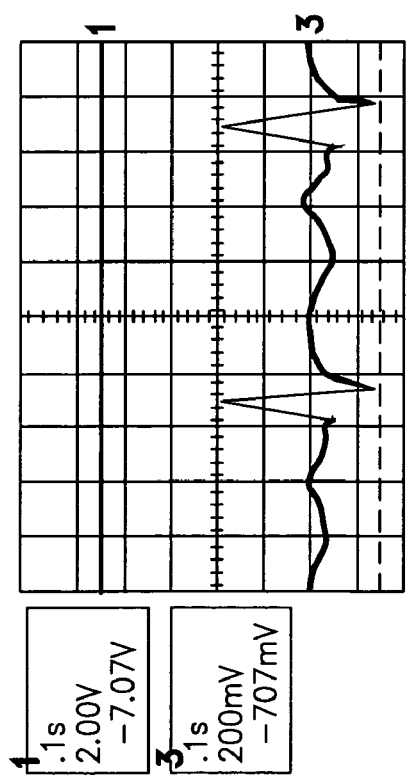

APPARATUS AND METHOD FOR REMOVING MAGNETIC RESONANCE IMAGING-INDUCED NOISE FROM ECG SIGNALS

CROSS REFERENCE TO RELATED APPLICATION

This application claims the benefit of U.S. Provisional Application Ser. No. 60/328,076, filed on Oct. 9, 2001, the contents of which are incorporated herein by reference.

BACKGROUND OF THE INVENTION

Magnetic Resonance Imaging (MRI) provides medical diagnostic information that can be difficult or impossible to obtain otherwise. This information often requires that the electrocardiogram (ECG) of the patient be monitored or measured during imaging. One reason for monitoring ECG signals is to synchronize the acquisition of images with the heart beat to, for example, reduce motion artifacts associated with the heart beat in the acquired images and to obtain dynamic images of the heart. Or, the patient may be so ill that his or her vital signs need to be monitored during the imaging procedure. Further, the effect of pharmacological stressors can be monitored via ECG signals. And, as medical science improves, other uses will be developed as well.

The ECG itself is a small electrical signal, on the order of millivolts, created by the nerves and muscles in the heart. The ECG signal is commonly sensed or detected by placing electrodes on the patient's chest. Wires from the electrodes carry the small electrical signals to an amplifier and other circuitry for ultimate display for health care professionals and for use by the MRI imaging system, for example, in synchronizing image acquisition in conjunction with the patient's heart beat.

However, the MRI equipment itself provides a very difficult environment for the measurement of these small signals. The wires are subject to changing magnetic fields, which can induce potentials in the wires that are orders of magnitude larger than the ECG. This noise or interference makes it difficult for the health care professional or the MRI imaging system to readily observe or monitor the patient's ECG.

The MRI equipment generates high power radio frequency (RF) magnetic fields, the exact frequency depending upon the steady state magnet strength (B0) and the atom being imaged. Generally the RF signals are in the megahertz (MHz) range. MRI scanners also include gradient coils that create magnetic field gradients across the volume of interest in the patient being imaged. Gradient fields are essential to the creation of the image. They can be switched on the order of a thousandth of a second, creating signals in the kilohertz (kHz) range. In addition, as stated above, the MRI scanner generates a very large steady state magnetic field (B0). As the wires are slowly moved through this field due to patient breathing or other motion, the change in flux can induce signals in the wires. While these signals are not steady voltages, the change can be so slow that the frequency is in the single digit Hertz (Hz) range.

The noise generated by and induced on the ECG signal by the RF magnetic field can be handled or removed from the ECG signal. High resistance leads, capacitors, and shunting diodes are commonly applied to the ECG acquisition circuitry to handle the RF magnetic field noise.

Several approaches are described in previous patents for addressing the gradient field noise issue, which is the most problematic in revealing the underlying ECG signals. Moore in U.S. Pat. No. 4,991,580 uses a slew rate limiting (SLR) circuit to reduce the gradient pulse amplitude while not reducing the ECG signal amplitude. Tsitlik et al in U.S. Pat. No. 5,217,010 utilize a secondary low pass filter or a band reject filter to similarly reduce the amplitude of the gradient noise pulse. Gober in U.S. Pat. No. 5,052,398 uses two fourth-order Butterworth filters. One is a low pass filter with a cutoff of 20 HZ. The second is a high pass filter with a cutoff of 10 Hz. An absolute value function filter then follows this Butterworth filter arrangement. Kreger et all in U.S. Pat. No. 5,436,564 use three (3) adaptive filters that receive an input from the MRI system's 3 gradient coil drivers. Blakeley et al. in U.S. Pat. No. 4,991,587 also utilize adaptive filtering. In a second patent, U.S. Pat. No. 5,038,785, Blakeley et al. utilize a sample and hold technique to remove the gradient pulses. The sample and hold technique works by recognizing that a gradient noise pulse is starting to occur and then holding the current ECG value until the gradient noise pulse has passed.

While each of these approaches may have been sufficient at the time they were invented, MRI systems continue to advance and improve. In the early 1990s, a temporal period on the order of seconds was typically required to acquire one MRI data set, and the gradients might only be switched a few times in that interval. Driven by the desire to have faster scans and acquire different types of information, there are significant trends toward faster gradient coil switching speeds. This increases the amplitude and frequency of the induced noise or interference. The other trend is to have the gradient coils activated or changed more frequently. Two examples of current sequences are FIESTA by General Electric Co. and FISP by Siemens, Inc. FIESTA has pulses with components in the kHz range with very fast rise time. In addition, perfusion imaging utilizes streams or bursts of gradient pulses.

These more "aggressive" protocols mean that solutions such as a sample and hold will begin to fail because there is less time to take a sample and more time required in the hold mode. The performance of the various strategies will also degrade as the number and amplitude of the gradient pulses increases. Specifically, the circuit of Moore in U.S. Pat. No. 4,991,580, the contents of which are hereby incorporated by reference, has a frequency response that has a higher gain for signals in the kilohertz range than at DC. This can cause it to function sub-optimally as gradient pulses become faster and more frequent.

SUMMARY OF THE INVENTION

The present invention broadly addresses the challenges in removing from ECG signals the gradient pulse interference or noise presented by the increased amplitude and frequency of newer and faster MRI gradient pulse sequences.

In a particular aspect, the present invention provides an improvement upon the circuit of Moore, U.S. Pat. No. 4,991,580. In the preferred arrangement, the present invention includes a single order low pass filter with a cutoff frequency of approximately 500 Hz positioned before the signal limiting circuit, one embodiment of which is the slew rate limiter (SLR) disclosed in Moore, U.S. Pat. No. 4,991,580. In the frequency domain this can be considered as overcoming the high gain that Moore's circuit has in the kHz range by attenuating the higher frequencies. In the time domain, it can be thought of as rounding the fast rise times of the gradient, in other words, making the rectangular gradient interference pulse more trapezoidal or triangular.

In another aspect, the present invention provides an apparatus and method for adapting or improving a conventional or existing ECG monitor. The MRI noise reduction circuitry present in the conventional or existing ECG monitor may be replaced, adapted or modified with the improved circuitry herein disclosed. The improved circuitry of the present invention may be provided or sold to owners of existing ECG monitors to improve the performance thereof.

Further aspects and attendant advantages of the present invention will be appreciated when the following detailed description of the invention is read in conjunction with the appended drawings.

BRIEF DESCRIPTION OF THE DRAWINGS

FIGS. 1, 2, 3 and 4 depict a prior art circuit from Moore U.S. Pat. No. 4,991,580 for removing MRI induced noise from an ECG signal.

FIGS. 6A–6H show comparative results of the circuitry of the present invention with and without the prefilter.

FIGS. 7A and 7B show the significantly improved behavior of the circuit with the prefilter.

DETAILED DESCRIPTION OF THE INVENTION

Figure 1:
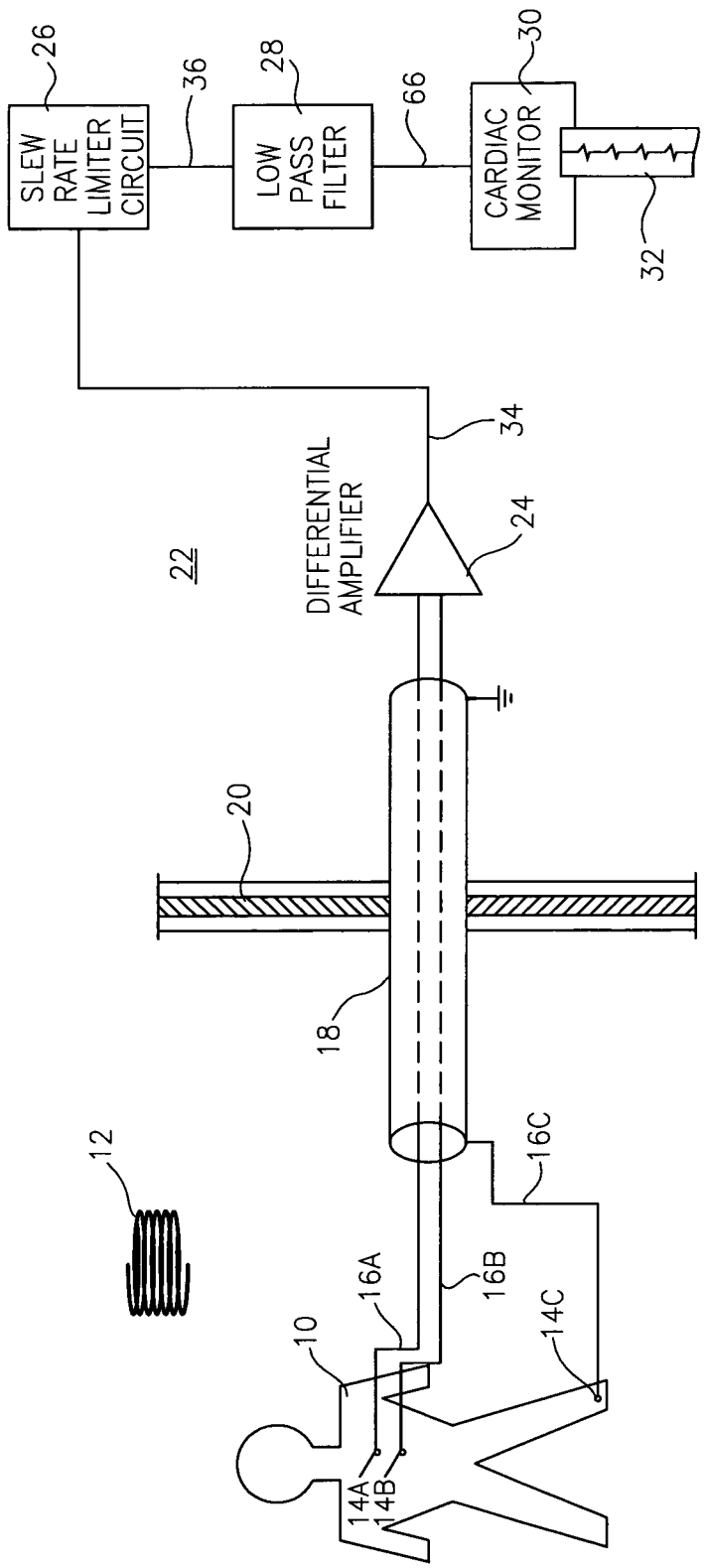

In a preferred and non-limiting embodiment, the present invention provides an improvement and expansion on U.S. Pat. No. 4,991,580 by John C. Moore, the contents of which are included herein by reference. FIGS. 1 though 4 from the Moore patent are reproduced as FIGS. 1 through 4 appended hereto.

Figure 5:
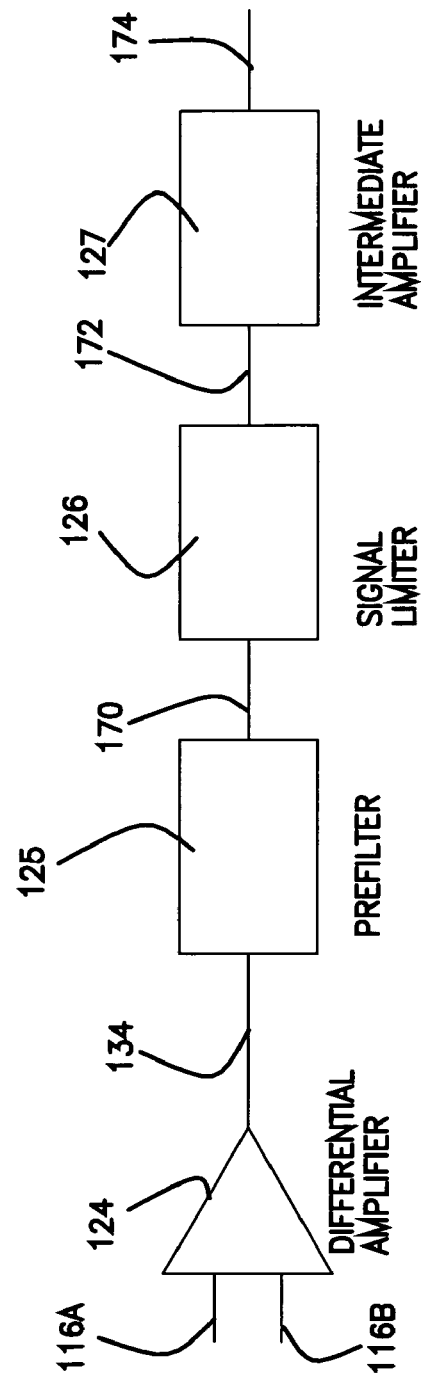
FIG. 5 is a block diagram of a preferred embodiment of the present invention.

FIG. 5 is a block diagram of the preferred embodiment of the present invention. 116A and 116B represent the ECG signal inputs that are corrupted with induced MRI interference or noise from a MRI imaging procedure. The differential amplifier 124 provides an output 134 that is a function of the difference between the two inputs while rejecting common mode signals. The gain is approximately 7. The prefilter 125 is preferably a single pole low pass filter with a cutoff frequency below that of the gradient induced noise in the thousands of Hertz range and well above the ECG signal frequencies of interest, which are in the tens of Hertz range. Preferable the filter has a cutoff of 80 Hz. Other more sophisticated filters can be used, but the simpler filter is described herein for example.

The output 170 of the prefilter 125 is the input to the signal limiter 126. The signal limiter of the preferred embodiment may be the slew rate limiting circuit of Moore, shown in FIG. 4. The Moore slew rate limiting circuit has a non-linear behavior, which will be discussed in more detail later. In effect it limits the amplitude of the gradient induced noise.

The present invention applies the output 172 of the signal limiter 126 to an intermediate amplifier 127 including an integral low pass filter. In the preferred embodiment, this circuit has a gain of 64 and a low pass filter preferably set at 40 Hz.

These two filters—the prefilter 125 and the integral low pass filter—significantly improve the behavior of the signal limiting circuit 126 and together they provide a patient ECG signal that is sufficient for scanner triggering or diagnosis even with more aggressive gradients and imaging protocols. The prefilter provides the greatest degree of improvement to the circuit. The integral low pass filter in the intermediate amplifier, in appropriate arrangements, may be optional.

One way to understand the drawback of Moore's SLR circuit is best understood by considering the gain versus frequency behavior. The circuit has a small signal gain (the ratio of the voltage at 36 to the ratio of the voltage at 34 in FIG. 4) of 1 at DC. And as the frequency of the signal increases, the impedance of capacitor 60 decreases. The maximum gain of the circuit is 105 with an upper breakpoint of approximately 1.6 kHz. This behavior is not a problem when noise from the gradients is large and infrequent, but as the gradient activation becomes more frequent or even continuously changing, this interferes with the ability of the circuit to transmit the ECG signal because the limiter will be almost continuously at one limit or the other. When this happens the R wave of the ECG is effectively attenuated.

Figure 8:
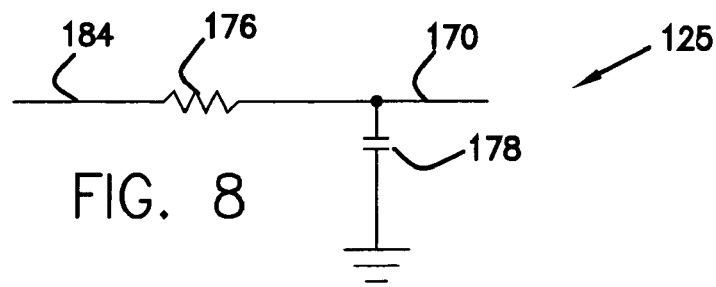
FIG. 8 is a diagram of an embodiment of the pre-limiter filter circuit of the present invention.

FIG. 8 shows the preferred embodiment of the prefilter 125. It is a single pole, low pass filter. The preferred value for resistor 176 is 20 kOhms. The preferred value for capacitor 178 is 0.1 uF (microfarad). This gives a 1/RC time constant of 500/sec. The prefilter effectively reduces the amplitude of all signals with a frequency greater than 80 Hz. Of course more sophisticated multi-pole filters could be used here. This circuit is preferred because it has been found to be sufficient to reduce the R wave attenuation. And, other design factors that have not been previously mentioned, such as size, power draw, complexity, and immunity to other sources of noise, tend to create a preference for simplicity.

Because of the practical design factors just mentioned, the preferred signal limiter 126 is not that of Moore U.S. Pat. No. 4,991,580, but that shown in FIG. 9. Operational amplifiers have improved since the early 1990's when Moore was working. The saturation behavior can be more symmetrical. By eliminating the Zener diode, the other diodes and a resistor, the size, cost and complexity is reduced. The theory of operation is still similar to Moore's. The slew rate limit is now set by the saturation voltage of the operational amplifier, the resistor 162, and the capacitor 160, since resistor 156 is significantly less than resistor 162. In the preferred embodiment, the resistor 162 has a value of 845 kOhms, resistor 156 is 393 ohms, and capacitor 160 is 0.1 uF.

Figure 9:
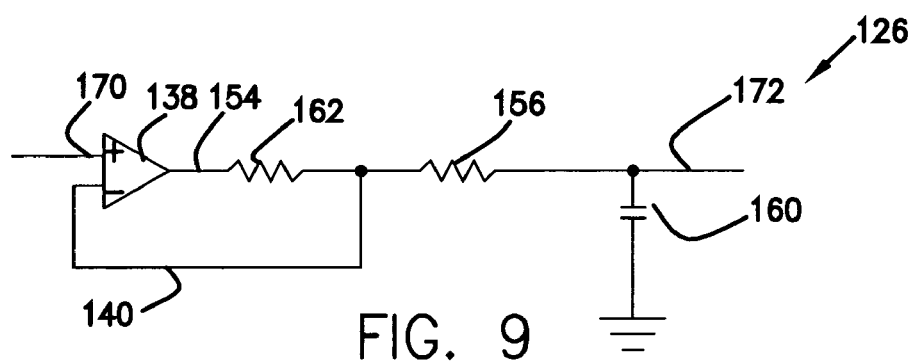
FIG. 9 is an embodiment of a signal limiting circuit of the present invention.

This circuit of FIG. 9 has a maximum gain of 2,150 and an upper breakpoint of approximately 4 kHz. Due to this, the performance of the signal limiter 126 is improved over Moore's SLR circuit (labeled 26 in FIG. 1). However, like the Moore circuit, it may still fail as the amplitude and rate of occurrence of the gradient noise increases.

A good way to reproducibly and efficiently simulate and demonstrate the ability to resist gradient noise and other noise above the ECG frequency of interest is to superimpose a square wave of 400 Hz on top of the ECG signal. Because of the fast rising and falling edges, a square wave has many high frequency components. This approximates the gradient pulses. FIG. 6 shows the measured result for several different amplitudes of square wave. FIGS. 6A through 6D illustrate the performance of the circuit with the following characteristics: the differential amplifier 124, bypassing the prefilter 125, and feeding directly to the signal limiter 126, followed by the intermediate amplifier 127 with an integral low pass filter. The circuit is then followed by a pulse width modulator, a fiber optic cable, and then a demodulator with a low pass filter. The circuit elements past the intermediate filter are known in the art and so are not described in further detail. They are all kept identical for all the measurements shown in FIGS. 6 & 7.

In 6A there is an ECG signal of amplitude 1 mV and no added noise. In 6B, the 400 HZ square wave noise has a peak-to-peak amplitude of 20 mV. This has not significantly reduced the amplitude of the R wave. In FIG. 6C, the amplitude of the noise is 25 mV and the peak of the R wave of the ECG has been reduced by 10%. This could have an effect on trigger for MRI synchronization. In FIG. 6D the noise amplitude is 75 mV. The R wave peak has been reduced by 50%, which is unsatisfactory.

FIGS. 6E through 6H show the same circuit arrangement as the measurements above with the inclusion of the prefilter 125 of the embodiment shown in FIG. 8 before the signal limiter 126. FIG. 6E has no noise, and so there is no R wave amplitude reduction. FIG. 6F has 20 mV of noise. Still no R wave amplitude reduction. FIG. 6G has 25 mV of noise. There is no R wave amplitude reduction. FIG. 6H shows no R wave reduction, even with 75 mV of noise. Without the prefilter, this amplitude of noise resulted in 50% reduction in R wave amplitude as shown in FIG. 6D.

FIG. 7A is identical to FIG. 6E. Both the prefilter 125 and the signal limiter 126 are present. The noise amplitude is 0 mV. FIG. 7B is that same circuit with a noise amplitude of 600 mV. Even with this amplitude of noise, the R wave is only reduced 10%. Thus the prefilter increases the amplitude of noise that can be tolerated by more than an order of magnitude.

As mentioned previously, there are two ways to understand this improvement. The first is in the frequency domain. The single pole low pass filter 125 provides attenuation of the noise signals on the ECG with a breakpoint of 80 Hz. This cancels the increasing gain that the signal limiting circuit 126 has as frequency increases. A second way is to consider the signal in the time domain. The low pass prefilter 125 rounds the edges of the 400 Hz noise, making it more triangular. This increases the time the amplifier operates in the linear mode when it is not saturated at the top or the bottom of its output range. This enables the level of the R wave of the ECG to be more faithfully transmitted through the limiting circuit 126.

Figure 10:
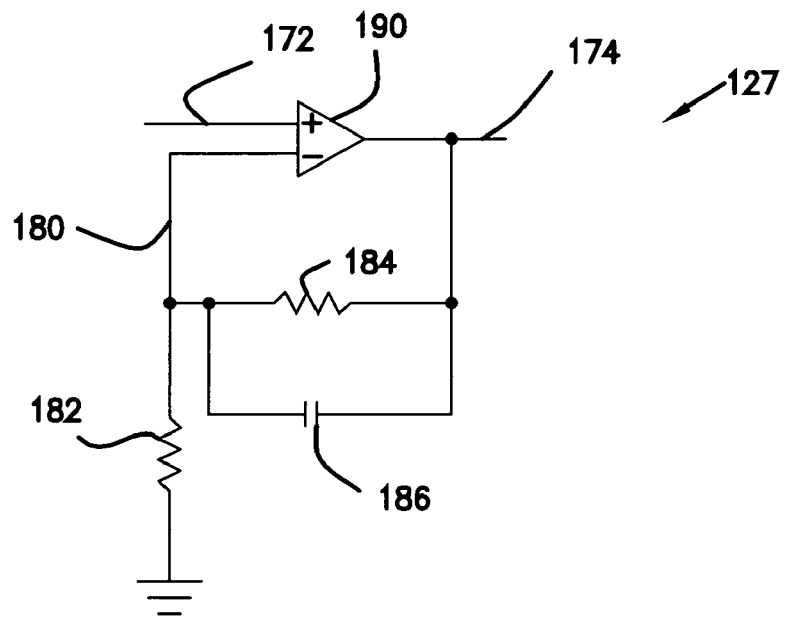
FIG. 10 is an embodiment of the intermediate amplifier of the present invention.

The preferred embodiment includes an intermediate amplifier 127 with an integral filter that follows the signal limiter 126. The circuit diagram for the intermediate amplifier 127 is shown in FIG. 10. It is a basic non-inverting amplifier with a single pole filter. Resistor 182 is preferably 13.3 kohms, resistor 184 is preferably 845 kOhms, and capacitor 186 is preferably 4700 pF. This provides a gain of 64 and a low pass breakpoint at about 40 Hz. This design provides additional filtering to further remove residual gradient or other noise, and is above any frequencies of interest in the ECG signal.

While it is envisioned that full ECG monitors will be built incorporating this circuit, it is also possible to build a module that incorporates the improvements disclosed herein and any necessary support circuitry such as power supplies so that currently used ECG monitors could gain the advantage of this invention without the owner having to purchase all new equipment.

The foregoing description and accompanying drawings set forth the preferred embodiments of the invention at the present time. Various modifications, additions and alternative designs will, of course, become apparent to those skilled in the art in light of the foregoing teachings without departing from the scope of the disclosed invention. For example, the component values can be varied or changed while still maintaining similar system performance. Further, performance characteristics such as specific cutoff frequencies or the number of poles in a filter may be varied or changed according to the application. The scope of the invention is indicated by the following claims rather than by the foregoing description. All changes and variations that come within the meaning and range of equivalency of the claims are to be embraced within their scope.

What is claimed is:

1. An apparatus for processing an ECG signal having MRI noise induced thereon, the apparatus comprising:
   (a) a differential amplifier;
   (b) a prefilter electrically connected to the differential amplifier;
   (c) a signal limiter circuit electrically connected to the prefilter; and
   (d) an intermediate amplifier electrically connected to the signal limiter, the intermediate amplifier comprising a low pass filter.

2. The apparatus of claim 1 wherein the differential amplifier has a gain of 7.

3. The apparatus of claim 1 wherein the prefilter is a single pole, low pass filter.

4. The apparatus of claim 1 wherein the prefilter has a cutoff frequency of approximately 80 Hz.

5. The apparatus of claim 1 wherein the low pass filter has a cutoff frequency of approximately 40 Hz.

6. The apparatus of claim 1 wherein the intermediate amplifier has a gain of 64.

7. A method of processing an ECG signal having MRI noise including RF magnetic field noise and gradient field noise induced thereon, the method comprising:
   (a) amplifying the ECG signal having MRI induced noise thereon;
   (b) prefiltering the ECG signal to remove at least a portion of the RF magnetic field noise therefrom;
   (c) signal limiting the ECG signal to remove at least a portion of the gradient field noise therefrom;
   (d) amplifying the ECG signal and further filtering therefrom frequencies above those of interest in the ECG signal.

8. A noise reduction circuit for use with an ECG monitor, the noise reduction circuit comprising:
   (a) a differential amplifier for amplifying a difference in electrical signals indicative of cardiac function to yield an ECG signal therefrom;
   (b) a prefilter electrically connected to the differential amplifier for filtering the ECG signal;
   (c) a signal limiter circuit electrically connected to the prefilter for removing high frequency noise from the ECG signal; and
   (d) an intermediate amplifier electrically connected to the signal limiter for amplification of the ECG signal received therefrom.

9. The noise reduction circuit of claim 8 wherein the differential amplifier has a gain of 7.

10. The noise reduction circuit of claim 8 wherein the prefilter is a single pole, low pass filter.

11. The noise reduction circuit of claim 8 wherein the prefilter has a cutoff frequency of approximately 500 Hz.

12. The noise reduction circuit of claim 8 wherein the intermediate amplifier further comprises a low pass filter for further removal of noise from the ECG signal.

13. The noise reduction circuit of claim 12 wherein the low pass filter has a cutoff frequency of approximately 500 Hz.

14. The noise reduction circuit of claim 1 wherein the intermediate amplifier has a gain of 64.

15. A method of adapting an ECG monitor equipped with a conventional noise reduction circuit, the method comprising the steps of:
   (a) providing a second noise reduction circuit, the second noise reduction circuit comprising (i) a differential amplifier, (ii) a prefilter electrically connected to the differential amplifier, and (iii) a signal limiter circuit electrically connected to the prefilter; and
   (b) electrically connecting the second noise reduction circuit to the ECG monitor.

16. The method of claim 15, further comprising the step of removing the conventional noise reduction circuit from the ECG monitor.

17. The method of claim 16 wherein the removal step occurs prior to the electrical connection step.

18. The method of claim 15 wherein the electrical connection step comprises electrically connecting at least a portion of the second noise reduction circuit to at least a portion of the conventional noise reduction circuit.

* * * * *